(12) United States Patent
Deane

(10) Patent No.: US 7,977,290 B1
(45) Date of Patent: *Jul. 12, 2011

(54) BODY CLEANSING COMPOSITION

(76) Inventor: Jeffrey Alan Deane, Los Angeles, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 12/479,602

(22) Filed: Jun. 5, 2009

Related U.S. Application Data

(60) Provisional application No. 61/059,248, filed on Jun. 5, 2008.

(51) Int. Cl.
*C11D 3/43* (2006.01)
*C11D 3/382* (2006.01)
*A61K 8/97* (2006.01)

(52) U.S. Cl. ......... 510/130; 510/131; 510/155; 424/401

(58) Field of Classification Search ................... 510/130, 510/131, 155; 134/401; 424/401
See application file for complete search history.

(56) References Cited

U.S. PATENT DOCUMENTS

| | | | | |
|---|---|---|---|---|
| 5,002,760 | A * | 3/1991 | Katzev | 424/59 |
| 6,312,675 | B1 * | 11/2001 | Deane | 424/70.1 |
| 6,723,309 | B1 * | 4/2004 | Deane | 424/70.1 |

OTHER PUBLICATIONS

Botanical Kinetics Purifying Creme Cleanser, Aveda, May 27, 2008, p. 1.*
"Botanical Kinetics™ Purifying Crème Cleanser," http://www.aveda.com/templates/products/sp.tmpl?CATEGORY_ID=CATEGORY10549&PRODUCT_ID=PROD6139, May 27, 2008 (1 page).
"Cleansers," http://www.cetaphil.com/Products/cleansers.aspx, May 27, 2008 (2 pages).

* cited by examiner

*Primary Examiner* — Brian P Mruk
(74) *Attorney, Agent, or Firm* — Blakely, Sokoloff, Taylor & Zafman, LLP

(57) ABSTRACT

A composition and method are provided. The composition is free of a non-botanical lathering agent and may include a botanical agent, a conditioning agent, a skin soothing agent, an antioxidant, an emulsifying agent, a chelating agent, and a preservative. The composition may be a skin cleansing composition free of a non-botanical lathering agent. The composition may be applied to the skin. The composition may be rinsed from the skin after it has remained on the skin for a period of time.

16 Claims, 1 Drawing Sheet

US 7,977,290 B1

BODY CLEANSING COMPOSITION

CROSS-REFERENCE TO RELATED APPLICATION

This application claims the benefit of U.S. provisional application Ser. No. 61/059,248, filed Jun. 5, 2008.

BACKGROUND

1. Field

Body cleansing compositions. More specifically, skin cleansing compositions.

2. Background

There are a wide variety of products on the market for cleaning and moisturizing, for example, skin on a user's body. Body cleansers include cleaning agents which are typically chemicals intended to remove dirt, oil, dead skin cells and other types of pollutants from the skin and/or hair. Such chemicals may include detergents and/or surfactants such as Sodium Lauryl Sulphate (SLS) or Sodium Laureth Sulphate (SLES). When applied to the skin and/or hair in combination with water, the cleansers provide a lathering effect. Many consumers associate lathering with cleaning therefore many cleansers include surfactants with strong lathering properties. These chemical cleaning agents, however, also strip the skin and hair of natural oils and moisture during the cleaning process.

BRIEF DESCRIPTION OF THE DRAWING

The embodiments herein are illustrated by way of example and not by way of limitation in the FIGURE of the accompanying drawing in which like references indicate similar elements. It should be noted that references to "an" or "one" embodiment in this disclosure are not necessarily to the same embodiment, and such references mean at least one.

DETAILED DESCRIPTION

Figure 1:
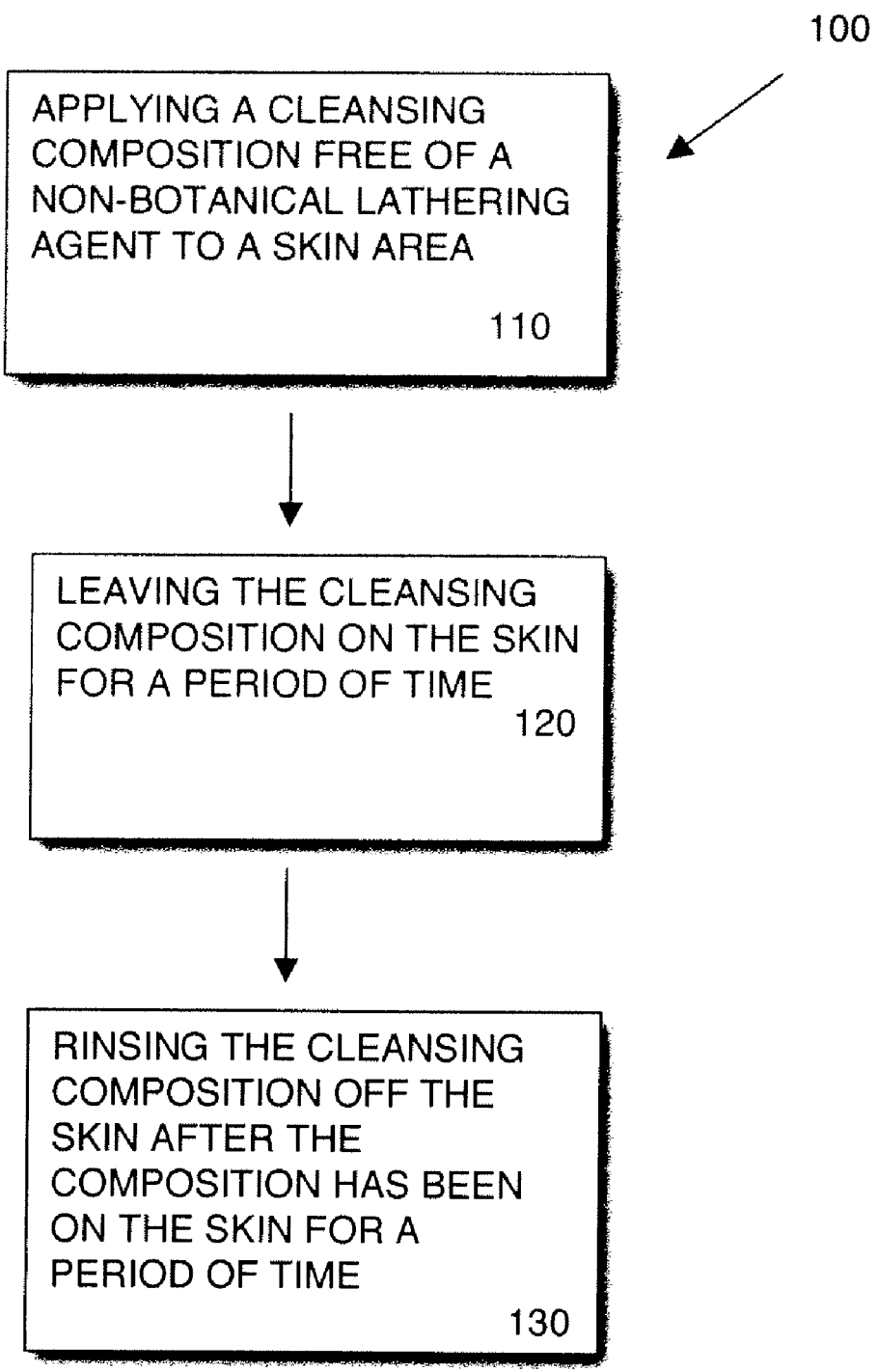
FIG. 1 is a flow chart of a method for applying a composition to the body.

In one embodiment, the body cleansing composition disclosed herein effectively cleans the body without the use of lathering agents or other non-botanical chemical agents known to deplete the skin of natural oils and moisture (e.g., SLS and SLES). In some embodiments, the cleansing composition is a non-lathering body cleansing composition that uses a blend of botanical agents that effectively clean the skin while leaving it soft and supple. The botanical agents in combination with other agents (e.g. antioxidants and conditioning agents) further diminish the appearance of fine lines and wrinkles. Accordingly, in addition to cleansing the skin, the composition may be used to treat age related skin conditions and achieve a more youthful complexion. The term "botanical agent" as used herein refers to plant derived products such as plant extracts. In this aspect, the terms "botanical agent" and "extract" are used interchangeably throughout the following description.

The composition is non-irritating and non-comedogenic such that it is suitable for use on all surfaces of the body including the face. In some embodiments, the composition is in the form of a body care product, including, without limitation, a cleanser, particularly a body cleanser. In some embodiments, the body cleanser is in the form of a cream, a scrub or a gel. The body cleanser may be in any form suitable for application to, and cleansing of, the skin. It is further contemplated that the cleanser may also effectively clean and/or moisturize other areas of the body, for example, hair on a user's head. In this aspect, the cleanser may be in any form suitable for application to, and cleansing of, the hair. In other embodiments, the composition is in the form of a lotion.

FIG. 1 is a flow chart of a method for applying a composition to the body. In some embodiments, to clean and/or moisturize the body using the composition, water is applied to an area of the body (e.g. the skin). A desired amount of the cleansing composition is then applied to the skin area (block 110). In some embodiments, the composition is applied by massaging it into the skin. It is further contemplated that an amount of the composition may be mixed with water, for example in the user's hand or on a sponge, and then massaged into the skin. Once applied to the skin, the composition may be left on the skin for a period of time (block 120). For example, the composition may be left on the skin for a period of from five to ten minutes. After the desired period of time, the composition may be removed from the skin. The composition may be removed from the skin after the period of time by, for example, rinsing the skin with water (block 130).

The composition includes a combination of botanical agents suitable for application to the skin. The botanical agents are included in the composition in amounts, which in combination, work synergistically to remove dirt and other unwanted contaminants from the skin without stripping the skin of its natural oils. Some of the botanical agents further add or restore moisture to the skin. The composition may further include agents such as solvents, conditioning agents, preservatives, skin soothing agents, antioxidants, emulsifying agents and chelating agents. In one embodiment, the composition balances one or more botanical cleansing agents with conditioning agents, skin soothing agents and antioxidants to provide a composition that effectively cleanses the skin and diminishes the appearance of fine lines and wrinkles. Representatively, a balanced composition includes from about 85.0 percent (%) to 95.0% by weight solvent, from about 0.25% to 1.0% by weight a botanical agent, from about 2.25% to 6.0% by weight a conditioning agent, from about 1.0% to 2.0% by weight a skin soothing agent and from about 0.5% to 1.5% by weight an antioxidant. The composition may further include from about 1.0% to 2.0% by weight an emulsifying agent, from about 0.05% to 0.1% by weight a chelating agent and from about 0.05% to 1.5% by weight a preservative. In other embodiments, the skin care composition can contain any of the agents disclosed herein, in any amounts and any combination.

In one embodiment, the botanical agent included in the composition may be *Saponaria Officinalis* Leaf/Root Extract. *Saponaria Officinalis* Leaf/Root Extract is derived from the vespertine flower and is more commonly known as Soapwort. Soapwort contains saponins that are naturally mild cleaning agents. In this aspect, when applied to the skin, the composition is able to clean the skin without the use of non-botanical synthetic chemical detergents and surfactants such as SLS and SLES typically found in cleansers. In addition, since agents such as SLS and SLES are not included in the composition, the composition cleans the skin without the drying effects typically caused by these synthetic chemical detergents and surfactants typically used in conventional cleansers. Soapwort is further recognized as having properties that regenerate, tone and soothe the skin.

It is contemplated that the composition may include other botanical agents that, in combination, facilitate cleansing and/or moisturizing of the skin. Representative other botanical agents may include, but are not limited to, *Aloe Barbadensis* Leaf Extract, *Lavandula Angustifolia* (Lavender) Oil,

*Lycium Chinense* Fruit (Goji Berry) Extract, *Camellia Sinensis* (White Tea) Leaf Extract, *Chamomilla Recutita (Matricaria)* Flower Extract, *Humulus Lupulus* (Hops) Extract, *Rosmarinus Officinalis* (Rosemary) Leaf Extract, *Achillea Millefolium* (Yarrow) Extract, *Cymbopogon Schoenanthus* (Lemongrass) Extract, *Melissa Officinalis* (Balm Mint) Leaf Extract and/or Wheat Germamidopropyldimonium Hydroxypropyl Hydrolyzed Wheat Protein.

It is recognized that some of the above botanical agents may clean and improve skin appearance due to their astringent, antiseptic and/or antioxidant properties.

Representative botanical agents having astringent properties which soothe the skin include, but are not limited to, *Humulus Lupulus* (Hops) Extract and *Achillea Millefolium* (Yarrow) Extract. *Humulus Lupulus* (Hops) Extract has astringent and anti-inflammatory properties that increase the strength and tone of veins. *Achillea Millefolium* (Yarrow) Extract has antibacterial and anti-inflammatory properties which clean the skin. Yarrow Extract further acts to balance and regulate sebaceous glands.

Representative botanical agents having antiseptic properties may include, but are not limited to, *Lavandula Angustifolia* (Lavender) Oil and *Cymbopogon Schoenanthus* (Lemongrass) Extract. *Lavandula Angustifolia* (Lavender) Oil soothes the skin and promotes healing and skin revival. In addition to antiseptic properties, Lavender Oil has antibacterial and anti-inflammatory properties. *Cymbopogon Schoenanthus* (Lemongrass) Extract is used in the composition as a cleanser that further soothes, tones and refreshes the skin and helps to control oily skin.

Representative botanical agents having antioxidant properties may include, but are not limited to, *Lycium Chinense* Fruit (Goji Berry) Extract, *Camellia Sinensis* (White Tea) Leaf Extract, *Rosmarinus Officinalis* (Rosemary) Leaf Extract and *Cymbopogon Schoenanthus* (Lemongrass) Extract. *Lycium Chinense* Fruit (Goji Berry) Extract contains nutrients that provide antioxidant benefits and protects the skin from sun damage and free radicals that can damage cells. *Camellia Sinensis* (White Tea) Leaf Extract boosts the immune function of skin cells to protect against sun damage. *Rosmarinus Officinalis* (Rosemary) Leaf Extract is an essential oil which softens, moisturizes and rejuvenates the skin. In addition to its antioxidant properties, *Rosmarinus Officinalis* (Rosemary) Leaf Extract has antibacterial and antifungal properties.

The composition may further include vitamins. In some embodiments, the vitamins have antioxidant properties that improve the user's complexion. Representative vitamins may include, but are not limited to, Tocopherol (Vitamin E), Tocopherol Acetate (Vitamin E), Tetrahexyldecyl Ascorbate (Vitamin C), Panthenol (Pro Vitamin B5) and Retinyl Palmitate (Vitamin A). Tocopherol (Vitamin E) is derived from wheat germ and/or vegetable oils. Tocopherol is an antioxidant that may be used in the composition to heal, rejuvenate, soften, sooth, protect and form a barrier to prevent moisture evaporation from the skin. Tocopherol also helps to soften the skin. Tocopherol Acetate (Vitamin E) is an antioxidant that helps prevent free radical damage to the skin and may form a barrier against moisture evaporation. Tetrahexyldecyl Ascorbate (Vitamin C) is an antioxidant that mitigates the damaging effects of ultraviolet exposure. Panthenol (Pro Vitamin B5) provides moisturizing and healing properties. Retinyl Palmitate (Vitamin A) is an antioxidant that stimulates skin rejuvenation and increases skin elasticity. In addition to promoting the healing of environmentally damaged skin (e.g., damage to the skin caused by the environment factors such as sun, wind and pollution), it is contemplated that the topical application of the above described agents having antioxidant properties may also help slow down the aging process and prevent wrinkles.

It is contemplated that other non-vitamin agents having antioxidant properties may have a beneficial effect on the skin and therefore may be included in the composition. For example, another suitable agent with antioxidant properties that may be included in the composition is açaí palm. Extracts from the fruit of aÅaí palm may be included in any amount suitable for improving skin appearance.

The composition may further include one or more conditioning agents believed to improve the appearance of the skin. For example, the composition may include hydrolyzed collagen from marine kelp. Hydrolyzed collagen is a protein that helps the skin look firm and provides moisturizing benefits. Other conditioning agents may include, but are not limited to, Behentrimonium Methosulfate, Cetearyl Alcohol, Myristamidopropyl Dimethylamine Phosphate, Wheat Germamidopropyldimonium Hydroxypropyl Hydrolyzed Wheat Protein, Glycerin, Butylene Glycol, Carbomer, Polysorbate 20, Palmitoyl Oligopeptide, Palmitoyl Tetrapeptide-7, Phytantriol, Panthenol and Retinyl Palmitate. Glycerin is a humectant derived from plants. Butylene Glycol is a humectant and emollient extracted from the Kava-Kava plant. Palmitoyl Oligopeptide is a conditioning agent which enhances the production of collagen, moisturizes and softens the skin. Palmitoyl Oligopeptide further includes cleansing properties. Palmitoyl Tetrapeptide-7 is a conditioning agent which increases skin elasticity, firmness and tone.

The composition is non-comedogenic and therefore does not contain pore-clogging agents that could lead to acne. The composition may also include acne treatment agents. Representative acne treatment agents may include agents previously disclosed, for example, *Aloe Barbadensis* Leaf Extract, Tocopherol (Vitamin E) and Retinyl Palmitate (Vitamin A) may treat acne. Other acne treatment agents included in the composition may be, but are not limited to, beta hydroxy acid (BHA), Green Tea Extract, Tea Tree Oil, Tea Tree Extract and/or *Prunella Vulgaris* Extract.

The composition may further include naturally occurring agents that protect the skin from ultraviolet (UV) rays (e.g. UVA and/or UVB) by absorbing, reflecting, or scattering the rays on the skin. For example, the composition may include the naturally occurring oxide of titanium, namely titanium dioxide, which scatters UV rays away from the skin. It is further contemplated that some of the antioxidants included in the composition may protect the skin from UV rays. The compositions provided herein can contain a variety of optional ingredients, including, without limitation, plant derived fragrances, colorants and the like, without departing from the principles taught herein.

Other agents included in the composition that are not specifically discussed above (e.g., solvents, emulsifying agents, chelating agents and preservatives), are included and described in reference to the exemplary formulation set forth below.

In one embodiment, the composition may be formed by combining two or more of the following agents: Water (Aqua), Behentrimonium Methosulfate, Cetearyl Alcohol, Cetyl Alcohol, Myristamidopropyl Dimethylamine Phosphate, *Aloe Barbadensis* Leaf Extract, *Saponaria Officinalis* (Soapwort) Leaf/Root Extract, *Lavandula Angustifolia* (Lavender) Oil, *Lycium Chinense* Fruit (Goji Berry) Extract, *Camellia Sinensis* (White Tea) Leaf Extract, Hydrolyzed Collagen (Marine Kelp), Panthenol (Vitamin B5), Retinyl Palmitate (Vitamin A), Tetrahexyldecyl Ascorbate (Vitamin C), Tocopherol (Vitamin E), Glycerin, Butylene Glycol, Carbomer, Polysorbate 20, Palmitoyl Oligopeptide, Palmitoyl Tetrapeptide-7, *Chamomilla Recutita (Matricaria)* Flower Extract, *Humulus Lupulus* (Hops) Extract, *Rosmarinus Offi-* cinalis (Rosemary) Leaf Extract, *Achillea Millefolium* (Yarrow) Extract, *Cymbopogon Schoenanthus* (Lemongrass) Extract, *Melissa Officinalis* (Balm Mint) Leaf Extract, Tocopherol Acetate (Vitamin E), Wheat Germamidopropyldimonium Hydroxypropyl Hydrolyzed Wheat Protein, Phytantriol, Disodium EDTA, Phenoxyethanol and Methylisothiazolinone.

Cetyl Alcohol is a humectant that inhibits moisture loss from the skin. *Chamomilla Recutita* (*Matricaria*) Flower Extract is an anti-inflammatory agent that soothes the skin. *Humulus Lupulus* (Hops) Extract has astringent and anti-inflammatory properties. *Melissa Officinalis* (Balm Mint) Leaf Extract soothes the skin. Disodium EDTA is a chelating agent that binds to metals, preventing them from reacting with compounds in the body. Phenoxyethanol and Methylisothiazolinone are preservatives.

In one embodiment, the composition may be formed as a cream composition having a specific gravity (SG) of 0.97, a pH of 4.66 and a viscosity of 40,000. The composition may be formed by heating the hydrophilic components to a temperature of 70 degrees Celsius. Hydrophobic components may further be heated to a temperature of 70 degrees Celsius. Each of the components used in the composition may be obtained from commercial sources. The heated hydrophilic and hydrophobic components may be combined while mixing with medium sheer. The mixture may be cooled to 40 degrees Celsius and any heat sensitive ingredients added. The cooled mixture with heat sensitive ingredients added may then be mixed until homogenous at room temperature.

In one embodiment the composition may have the following exemplary formulation:

| INGREDIENT | FUNCTION | SOURCE | PERCENT |
| --- | --- | --- | --- |
| Water | Solvent | CTFA | 88.00-94.00% |
| Behentrimonium Methosulfate, Cetearyl Alcohol | Conditioning Agent | CTFA | 1-3% |
| Cetyl Alcohol | Emulsifying Agent | CTFA | 1-2% |
| Myristamidopropyl Dimethylamine Phosphate | Conditioning Agent | CTFA | 1-2% |
| *Lavandula Angustafolia* (Lavender) Oil | Skin Soother | CTFA | 1-2% |
| Phenoxyethanol | Preservative | CTFA | 0.5-1% |
| Tocopherol Acetate | Antioxidant | CTFA | 0.5-1% |
| Wheat Germamidopropyldimonium Hydroxypropyl Hydrolyzed Wheat Protein | Conditioning Agent | CTFA | 0.25-0.5% |
| *Chamomilla Recutita* (*Matricaria*) Flower Extract, *Achillea Millefolium* (Yarrow) Extract, *Cymbopogon Schoenanthus* (Lemongrass) Extract, *Humulus Lupulus* (Hops) Extract, *Rosmarinus Officinalis* (Rosemary) Leaf Extract, *Melissa Officinalis* (Balm Mint) Leaf Extract | Extract | CTFA | 0.25-0.5% |
| Disodium EDTA | Chelating Agent | CTFA | 0.05-0.1% |
| Phytantriol | Conditioning Agent | CTFA | 0.05-0.1% |
| Methylisothiazolinone | Preservative | CTFA | 0.05-0.1% |
| Glycerin, Butylene Glycol, Carbomer, Polysorbate 20, Palmitoyl Oligopeptide, Tetrapeptide-7 | Conditioning Agent | CTFA | 0.05-0.1% |
| Panthenol | Conditioning Agent | CTFA | 0.01-0.05% |
| Collagen | Conditioning Agent | CTFA | 0.01-0.05% |
| *Aloe Barbadensis* Leaf Extract | Extract | CTFA | 0.01-0.05% |
| *Saponaria Officinalis* (Soapwort) Leaf/Root Extract | Extract | CTFA | 0.01-0.05% |
| *Camellia Sinensis* Leaf Extract | Extract | CTFA | 0.01-0.05% |
| *Lycium Chinese* Fruit Extract | Extract | CTFA | 0.01-0.05% |
| Tocopherol | Antioxidant | CTFA | 0.01-0.05% |
| Tetrahexyldecyl Ascorbate | Antioxidant | CTFA | 0.01-0.05% |
| Retinyl Palmitate | Conditioning Agent | CTFA | 0.01-0.05% |

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawing are, accordingly, to be regarded in an illustrative rather than a restrictive sense.

The invention claimed is:

1. A composition comprising:
88.0% to 95.0% by weight a solvent;
0.29% to 0.7% by weight a botanical agent;
2.38% to 5.85% by weight a conditioning agent;
1.0% to 2.0% by weight a skin soothing agent;
0.52% to 1.1% by weight an antioxidant;
1.0% to 2.0% by weight an emulsifying agent;
0.05% to 0.1% by weight a chelating agent; and
0.55% to 1.1% by weight a preservative;

wherein the composition is free of a non-botanical lathering agent.

2. The composition of claim 1 wherein the composition is a skin cleansing composition.

3. The composition of claim 1 wherein the botanical agent is a cleansing agent.

4. The composition of claim 1 wherein the botanical agent is selected from the group consisting of *Saponaria Officinalis* (Soapwort) Leaf/Root Extract, *Aloe Barbadensis* Leaf Extract, *Lavandula Angustifolia* (Lavender) Essential Oil, *Lycium Chinense* Fruit (Goji Berry) Extract, *Camellia Sinensis* (White Tea) Leaf Extract, *Chamomilla Recutita* (*Matricaria*) Flower Extract, *Humulus Lupulus* (Hops) Extract, *Rosmarinus Officinalis* (Rosemary) Leaf Extract, *Achillea Millefolium* (Yarrow) Extract, *Cymbopogon Schoenanthus* (Lemongrass) Extract and *Melissa Officinalis* (Balm Mint) Leaf Extract.

5. The composition of claim 1 wherein the skin soothing agent is *Lavandula Angustafolia* (Lavender) Oil.

6. The composition of claim 1 wherein the conditioning agent is selected from the group consisting of Hydrolyzed Collagen from Marine Kelp, Behentrimonium Methosulfate, Cetearyl Alcohol, Myristamidopropyl Dimethylamine Phosphate, Wheat Germamidopropyldimonium Hydroxypropyl Hydrolyzed Wheat Protein, Phytantriol, Glycerin, Butylene Glycol, a polymer of Acrylic Acid, Polysorbate 20, Palmitoyl Oligopeptide, Palmitoyl Tetrapeptide-7, Panthenol and Retinyl Palmitate.

7. The composition of claim 1 wherein the antioxidant is a vitamin selected from the group consisting of Vitamin C and Vitamin E.

8. A composition comprising:
a skin cleansing composition free of a non-botanical lathering agent, the composition comprising 0.52% to 1.1% by weight an antioxidant and *Saponaria Officinalis* (Soapwort) Leaf/Root Extract.

9. The composition of claim 8, wherein the skin cleansing composition comprises a botanical agent.

10. The composition of claim 8, wherein the skin cleansing composition comprises an antiseptic.

11. The composition of claim 8, wherein the skin cleansing composition comprises an astringent.

12. The composition of claim 8, wherein the skin cleansing composition comprises hydrolyzed collagen.

13. A composition comprising:
88.00% to 94.00% by weight water;
1.0% to 3.0% by weight one of Behentrimonium Methosulfate or Cetearyl Alcohol;
1.0% to 3.0% by weight Cetyl Alcohol;
1.0% to 2.0% by weight Myristamidopropyl Dimethylamine Phosphate;
1.0% to 2.0% by weight Lavandula Angustafolia (Lavender) Oil;
0.5% to 1.0% by weight Phenoxyethanol;
0.5% to 1.0% by weight Tocopherol Acetate;
0.25% to 0.5% by weight Wheat Germamidopropyldimonium
Hydroxypropyl Hydrolyzed Wheat Protein;
0.25% to 0.5% by weight an extract selected from the group consisting of *Chamomilla Recutita* (*Matricaria*) Flower Extract, *Achillea Millefolium* (Yarrow) Extract, *Cymbopogon Schoenanthus* (Lemongrass) Extract, *Humulus Lupulus* (Hops) Extract, *Rosmarinus Officinalis* (Rosemary) Leaf Extract and *Melissa Officinalis* (Balm Mint) Leaf Extract;
0.05% to 0.1% by weight Disodium EDTA;
0.05% to 0.1% by weight Phytantriol;
0.05% to 0.1% by weight Methylisothiazolinone;
0.05% to 0.1% by weight a conditioning agent selected from the group consisting of Glycerin, Butylene Glycol, a polymer of Acrylic Acid, Polysorbate 20, Palmitoyl Oligopeptide and Tetrapeptide-7;
0.01% to 0.05% by weight Panthenol;
0.01% to 0.05% by weight Collagen;
0.01% to 0.05% by weight Aloe Barbadensis Leaf Extract;
0.01% to 0.05% by weight *Saponaria Officinalis* (Soapwort) Leaf/Root Extract;
0.01% to 0.05% by weight *Camellia Sinensis* Leaf Extract;
0.01% to 0.05% by weight *Lycium Chinense* Fruit (Goji Berry) Extract;
0.01% to 0.05% by weight Tocopherol;
0.01% to 0.05% by weight Tetrahexyldecyl Ascorbate; and
0.01% to 0.05% by weight Retinyl Palmitate.

14. A method comprising:
applying a cleansing composition free of a non-botanical lathering agent to a skin area, wherein the composition comprises;
88.0% to 95.0% by weight a solvent;
0.29% to 0.7% by weight a botanical agent;
2.38% to 5.85% by weight a conditioning agent;
1.0% to 2.0% by weight a skin soothing agent;
0.52% to 1.1% by weight an antioxidant;
1.0% to 2.0% by weight an emulsifying agent;
0.05% to 0.1% by weight a chelating agent; and
0.55% to 1.1% by weight a preservative.

15. The method of claim 14 further comprising:
leaving the cleansing composition on the skin for a period of time.

16. The method of claim 15 further comprising:
rinsing the cleansing composition off the skin after the composition has been on the skin for the period of time.

* * * * *